United States Patent
Kara

[11] Patent Number: 6,088,695
[45] Date of Patent: Jul. 11, 2000

[54] SYSTEM AND METHOD FOR COMMUNICATING MEDICAL RECORDS USING BAR CODING

[76] Inventor: Salim G. Kara, 17 Bayview Forest Lane, Markham, Ontario, Canada, L3T7S4

[21] Appl. No.: 08/715,185

[22] Filed: Sep. 17, 1996

[51] Int. Cl.[7] .................................................. G06F 17/30
[52] U.S. Cl. ................................................. 707/10; 705/3
[58] Field of Search ......................... 705/3; 395/200.47; 369/69; 380/24; 707/10

[56] References Cited

U.S. PATENT DOCUMENTS

| | | | |
|---|---|---|---|
| 5,267,314 | 11/1993 | Stambler | 380/24 |
| 5,319,543 | 6/1994 | Whilhelm | 705/3 |
| 5,321,681 | 6/1994 | Ramsay et al. | 369/69 |
| 5,485,370 | 1/1996 | Moss et al. | 395/200.47 |
| 5,684,288 | 11/1997 | Renvall | 235/462 |

*Primary Examiner*—Mark R. Powell
*Assistant Examiner*—John L. Young
*Attorney, Agent, or Firm*—Fulbright & Jaworski L.L.

[57] ABSTRACT

A system and method for coding data into physical form and for delivering the coded data to a recipient for entering the data into a form controlled by the recipient. One embodiment of the coded data is medical data generated by a plurality of different care providers and the recipient is a primary care provider. The medical data is coded in a uniform manner, such as a bar code, and is easily transported and stored, both in physical and electronic form.

24 Claims, 2 Drawing Sheets

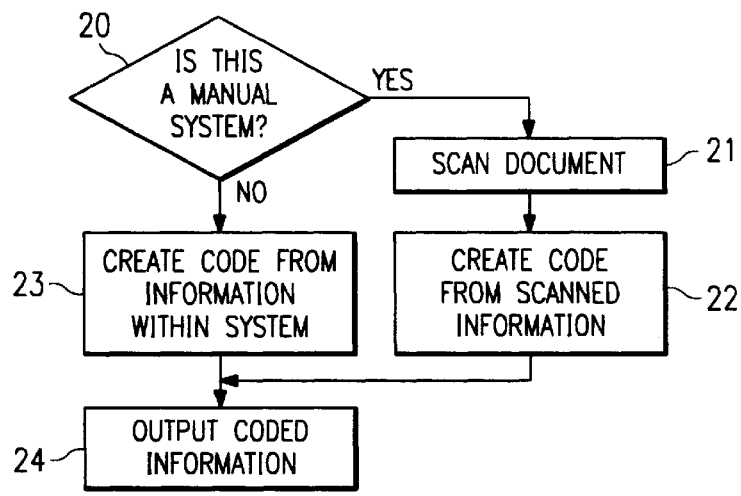
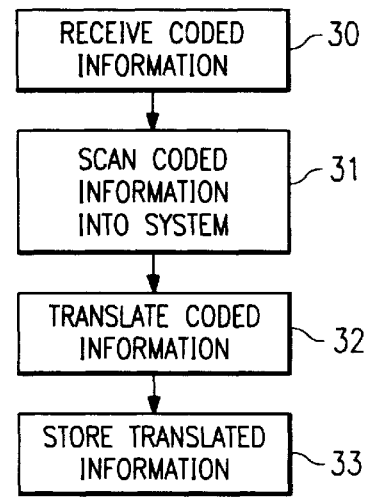
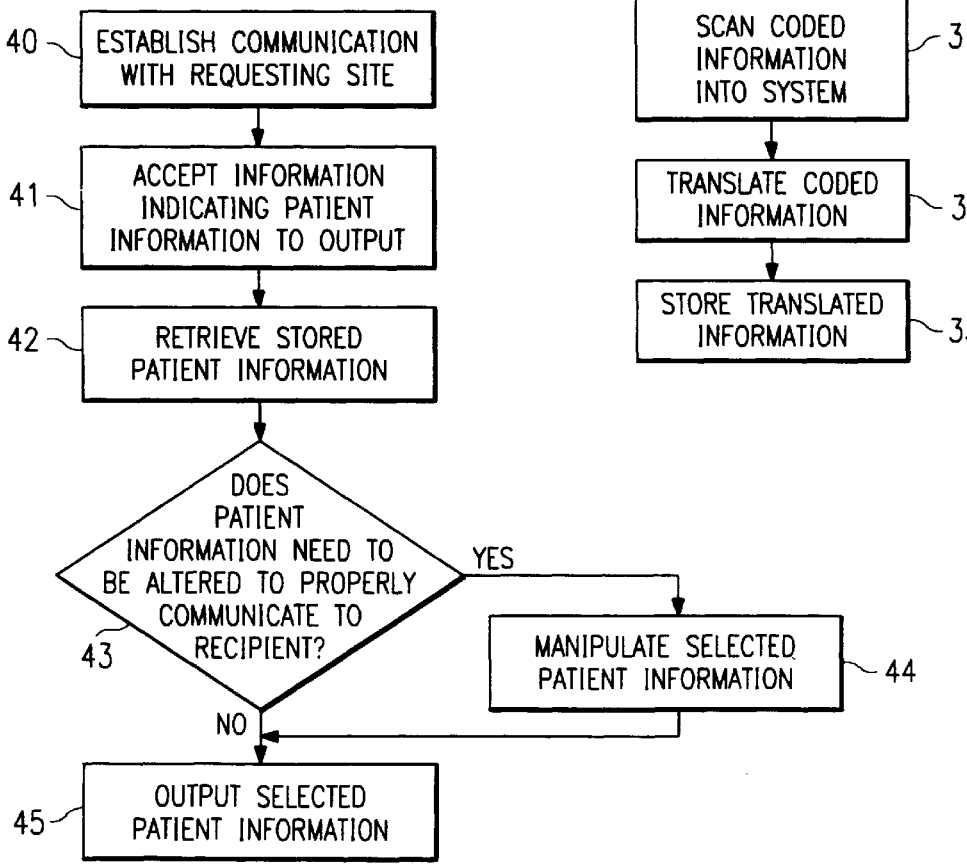

SYSTEM AND METHOD FOR COMMUNICATING MEDICAL RECORDS USING BAR CODING

REFERENCE TO RELATED APPLICATIONS

The present application is being concurrently filed with U.S. application Ser. No. 08/710,499, entitled "METHOD AND SYSTEM FOR TRANSFER OF DATA FROM ONE LOCATION TO ANOTHER" and U.S. application Ser. No. 08/710,523, entitled "SYSTEM AND METHOD FOR COMMUNICATING SENSITIVE DATA," each having a common inventor, which applications are hereby incorporated by reference.

TECHNICAL FIELD OF THE INVENTION

This invention relates to a system and method for storing and communicating records and more particularly to an arrangement whereby such records can be stored in a secure fashion and communicated from one location to another in a private manner and with a minimum of risk from error.

BACKGROUND OF THE INVENTION

In many professions it is necessary to maintain extensive data records which extend over a period of years. Often these records are generated at a variety of different physical locations, under a variety of different conditions, stored in different physical locations, and accessed at different times by different people for different reasons. A good example of such a situation now exists in the medical profession where a patient's medical history spans a large number of years, is usually generated by several different physicians working in cooperation with several different laboratories and diagnostic centers.

While it would be ideal to believe that there is one care provider who maintains all of these diverse records, the reality is that this is simply not so. However, even if it were to be true that there is a central depository for the medical records of a patient, simply moving the data from the inception source to the storage location is a hugh task fraught with the possibility of errors, not to mention the time delay involved with the physical copying and transporting of each record. Often in emergency situations, where time is scarce, a physician must have immediate access to data contained on a graph or from a pictorial image that is physically resident at a remote site, such as the MRI facility of a hospital. In such a situation, the physician must rely on someone else to interpret the data over a telephone connection. Because of the unexpected nature of certain medical conditions, the timing is not always convenient to retrieve documents which are stored remotely from the attending physician and, thus, valuable time is lost and medical treatment must be rendered based upon a best guess scenario.

It is not uncommon for a patient who has undergone a series of tests to have to wait a week or more before the test results are gathered by the diagnosing physician so that the physician can then make a proper diagnosis. In some situations the patient's condition could have changed dramatically in such a time. It is not unheard of that test results have been lost or damaged before they reach the proper care provider.

One answer to such a situation is to place a large majority of the diagnostic facilities and laboratories in or near a common facility, such as a hospital, and to confine the patient to the hospital while all of the tests are run. In addition to being very costly, and perhaps effective for true emergency situations, this system does not resolve the issue of moving the gathered data to the different people who must then have immediate access to the data. Because of the high cost of medial care there is usually a third party, such as an insurance company or a medical board of review, who must also have immediate and concurrent access to the data in order to approve of a certain course of treatment.

Accordingly, there is a need in the art for a broadly accepted system for storing records and for communicating these stored records to and from a number of different locations.

There is a further need in the art for a system where medical records are stored in a manner such that they can be retrieved at any time from any location by the person who requires access to the records, such retrieval being accomplished in real time and in a secure manner.

SUMMARY OF THE INVENTION

These and other objects, desires and features have been achieved with a system and method which allows a creator of information to encode the information for subsequent transmission to, and storage by, a central facility. Thereafter the central facility provides the information to requesting parties. Provision of this information by the central storage facility may be in a number of formats depending on the needs of the recipient.

For example, where the information is patient information, a doctor initially creates the patient information in the usual manner. This information may be textual, such as records as to symptoms and diagnosis, or may be graphical, such as radiographic images of the patient. Once the doctor creates the patient information in the usual way, it is then encoded utilizing a coding method compatible with the central facility, such as that of the patient's primary care provider.

The coding method may be, for example, a bar code representation of the information so encoded. After coding by the physician, the coded patient information is transmitted to the central facility for storage and subsequent dissemination.

The information as coded includes information as to a particular patient with which it is associated. Furthermore, as the information may be provided in an intelligent fashion, and not simply in batch, information identifying the type of information, such as, for example, radiographic image or dental record, may also be included. This identification information may be quite detailed and may even comprise a predetermined categorization scheme to allow for the rapid retrieval of very specific pieces of information.

The coding method adopted may proscribe a format in which the information is to be presented. For example, all information related to a particular identified transaction may be coded in a predetermined sequence to enable the central facility to more readily assimilate the information into its storage banks. Such a predefined format of information presentation may be utilized to eliminate the transmission of additional information, not related to the patient records, necessary to identify the particular information that is being transmitted. Furthermore, such a predefined format may enable the precise identification, by the system, of the information transmitted, as the format may define particular locations, or cells, in which information suitable for such a determination may be found. Therefore, simply by presenting the patient information in a predetermined way, rapid access to very specific pieces of the stored information may be provided without the need for any additional information management data. As such, more efficient use of available transmission bandwidth is made.

Transmission of the coded information may be by any means deemed advantageous. For example, the coded information may be transmitted by postal service or hand, if desired. However, it shall be appreciated that electronic transmission of the encoded data, such as coupling processor-based systems through a public switched network (PSN), may result in a more rapid transmission.

Once received by the central storage facility, regardless of the method by which it was communicated, the patient information is stored electronically in a memory system accessible to a processor-based system. The information so stored may be indexed and sorted according to any number of methods well known in the art to provide meaningful access to its contents.

In addition to providing storage and cataloging of the information stored, the central storage facility storage system provides a method of dissemination of the stored information compatible with various user devices. For instance, as the information is electronically stored, access to the information may be provided by the linking of a computer system at the recipient's site to that of the central facility. The presentation of the information might be multimedia, as is well known in the art.

However, to enable the distribution of this information in the most possible situations, the information, as stored electronically, may also be provided by less conventional methods. For example, a doctor treating a patient who's records are stored by a central storage facility may not have means at his/her disposal to link a computer system, capable of browsing the stored information, with that of the central storage facility. Therefore, the central storage facility may transmit the information to the recipient without the linking of computers, but rather through transmission of a facsimile image of the information, for example. Here the information may be received by a facsimile device at the recipient's site and printed as a physical copy of the information.

This hard copy may take the form of machine readable code, such as a bar code. The bar code may then be input into the recipient's computer for decoding and presentation in human understandable form.

Moreover, the hard copy may initially take the form of human understandable information. Here the recipient may indicate to the central storage facility that human understandable information is required, and the central storage facility retrieves the information and manipulates it into a format to result in a human readable version being output at the recipient's site. Such manipulation may involve the rearranging of information stored, integration of various cells of information stored, or may even include the appending of certain static information, such as header information, to aid the recipient in understanding the transmitted information.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which:

FIG. 2 shows a flow chart of the operation of the information coding phase of the present invention;

FIG. 3 shows a flow chart of the receipt and storage of information by a central storage facility of the present invention; and FIG. 4 shows a flow chart of the retrieval and output of stored information by a central storage facility of the present invention.

DESCRIPTION OF THE PREFERRED EMBODIMENTS

Figure 1:
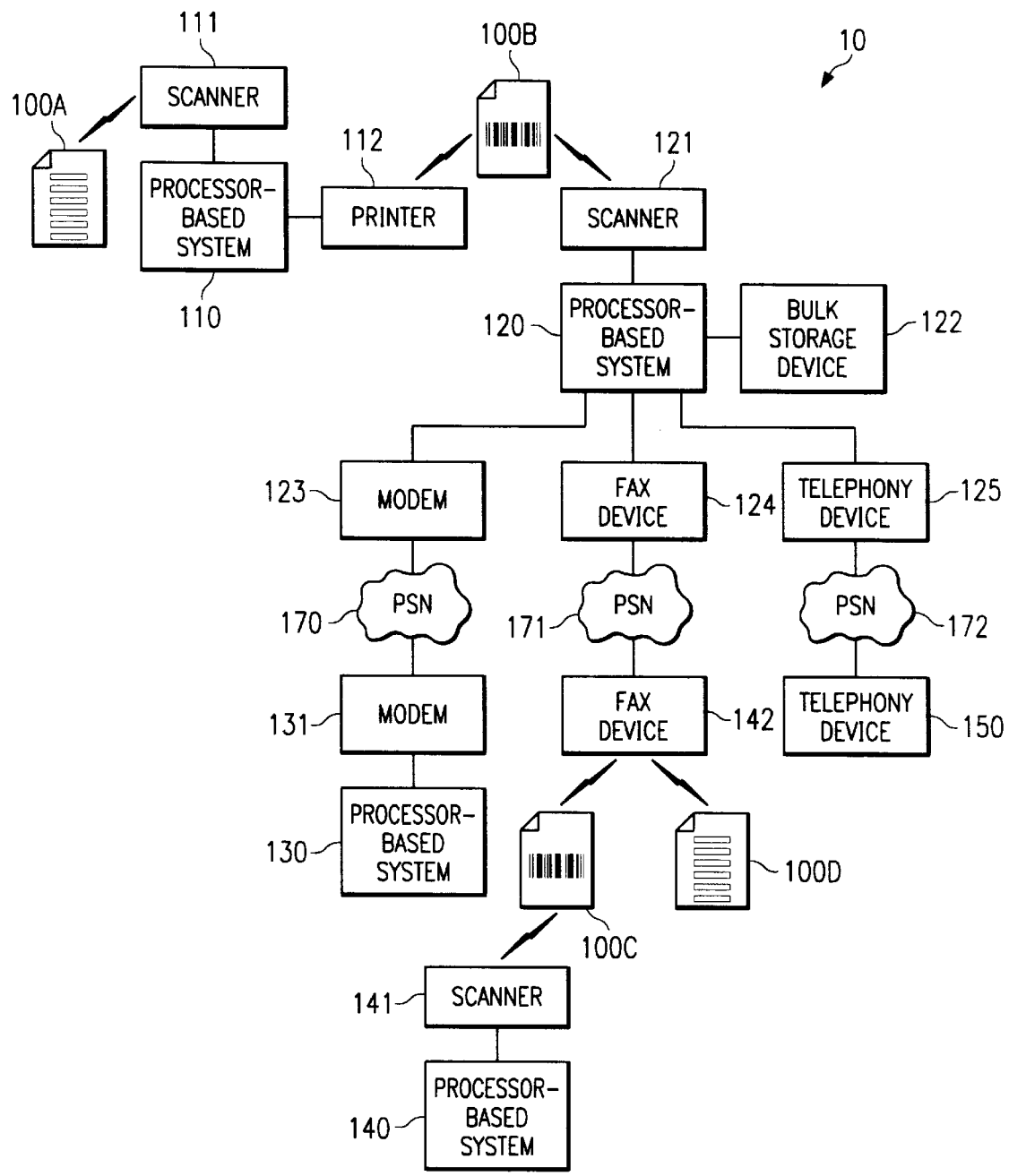
FIG. 1 shows an overview of the system and method of the present invention.

Directing attention to FIG. 1, there is shown an overview 10 of the system and method of the present invention, in which the original patient information document 100A is shown in conventional (human understandable) form and in which coded document 100B is shown with the information in a coded form such as, for example, a bar coded format.

In document 100A there may be included various information, such as identification of the patient to which it is associated, symptoms of a condition, and a doctor's diagnosis. Document 100A is not limited to textual information and may include graphical information such as a radiograph or an MRI scan. Moreover document 100A may include a combination of graphical and textual information.

The information contained in document 100A is input into processor-based system (PC) 110 through such means as scanner 111. Scanner 111 may have associated therewith an optical character recognition (OCR) system capable of converting a scanned image of textual information within document 100A to a form in which PC 110 may manipulate individual textual portions of the information. Of course, the information contained in document 100A may have been originally generated upon PC 110, or another processor-based system coupled thereto, and thus not necessitate its input.

The information originally contained in document 100A is output by PC 110, such as through printer 112, in coded form, as illustrated by document 100B. This coded version of the information is suitable for transmission to and subsequent input into a centralized processor-based system, such as PC 120. It shall be appreciated that coding of the information provides a convenient form in which to communicate the information as, in addition to providing for automated, and presumably error free, input into a central storage facility system, a code format may be selected which compresses the information. Furthermore, such coded information provides a limited amount of security as the information is not immediately understandable by a human. Of course, if additional security is desired the information may be encrypted in addition to being encoded.

Input may be through the use of scanner 121, as illustrated in FIG. 1, or may be by any other means capable of communicating the information into PC 120. For example, rather than inputting by scanner 121, the coded information may be input into PC 120 through the use of a coupled device such as modem 123 or fax device 124. Of course, where this information is input into PC 120 by other means, PC 110 may communicate the information electronically, through a compatible device, rather than physically outputting the information through printer 112.

After input of the information, PC 120 stores the information for later use or dissemination, such as on bulk storage device 122. Of course, prior to, or after, storage of the information, PC 120 may manipulate portions of the information to enable better use of the stored information. Additionally, PC 120 may also operate to index or organize the stored information to present it in a logical or expedient fashion.

As it is envisioned that PC 120 will receive such information from a number of different sources, information received by PC 120 may be altered from the form in which it is received prior to storage on bulk storage device 122. Such alteration may be to convert the information received from various sources, and therefore possibly in different formats, to a common format for storage and retrieval. Such alteration may involve, for example, the conversion of an image file initially digitized in one format, such as a PIF format, to a different digitized format, such as GIF.

Once stored and properly indexed or referenced, the information stored on bulk storage device may be disseminated by PC 120 to those requiring it. For example an emergency room technician may require a medical history of a trauma victim and contact the central storage facility, and thus PC 120, indicating the patient for which records are required as well as what records are needed.

It shall be appreciated that communication with PC 120 by the requesting party may be accomplished by any number of means capable of transferring the required information. For instance, in our emergency room example, the technician may cause PC 130 to initiate communication with PC 120 over public switched network (PSN) 170 through modems 131 and 123. Thereafter, PC 120 may respond with a user interface, as is well known in the art, allowing the technician to browse the patient's information.

In a preferred embodiment, PC 130 utilized for browsing information stored on PC 120 is capable of displaying both textual and graphical information. Furthermore, PC 130 may be adapted for audio presentation of information, such as is common in a multi-media computer system. However, it shall be understood that such a spectrum of display ability is not a requirement of PC 130 for use in the present invention. It is not uncommon for certain PCs, or other terminal equipment, to lack sufficient ability to display certain, or even any, graphical information. In these instances PC 120 may provide information suitable for causing PC 130 to output such non-displayable information to a coupled device, such as a printer (not shown). Furthermore, if no such alternate device is available, PC 120 may communicate what information can be displayed and indicate the availability of additional, non-compatible, information for dissemination by other means.

In another example of communication with PC 120, a non-interactive display device, such as fax device 142, may be utilized to present the requested information. For example, where the requesting party does not have at his/her disposal a computer system capable of interacting with PC 120, this person may contact PC 120 through PSN 172 utilizing telephony device 150 and telephony device 125. Telephony device 150 may be a standard telephone set with, for example, a dual tone multiple frequency (DTMF) keypad. Interaction with PC 120 may be accomplished by a voice processing unit (VPU) contained within telephony device 125 presenting voice prompts and responding to information communicated through DTMF signals. The requesting party may navigate a menu structure presented by PC 120 to select the precise information needed and indicate an electronic address, such as a phone number, to which to transmit the information. Thereafter, PC 120 may access bulk storage device 122, convert the stored information into a format suitable for presentation through the device indicated by the requesting party, and transmit the converted information.

Referring again to fax device 142 of our example, the information may be communicated through PSN 171 by fax device 124 coupled to PC 130 to ultimately be printed on fax device 142. As illustrated in FIG. 1, the output information may assume various forms. Document 100D, for example, is the requested information in human understandable form. This format may include certain information, not actually stored as patient information, useful in the requesting party's understanding of the information. For example, although only actual information regarding the particular patient may be stored on bulk storage device 122, document 100D may include certain header or caption information delineating the presented information. It shall be appreciated that document 100D may include graphical as well as textual information.

Document 100C is the requested information in coded form. This code may be decoded for presentation in human understandable fashion by the use of PC 140 having scanner 141 coupled thereto, for example. The coded information of document 100C may include coded versions of textual and graphical information and may also include certain information which is human understandable, such as, for example, instructions as to its use. The textual information encoded in document 100C may simply be the data associated with the particular patient, or may also include certain header or caption information as deemed necessary. It shall be understood that, if system 140 with which the requesting party is to decode this information is adapted specifically for receiving this type of information, there may be no need to communicate header or caption information in addition to the specific patient information. However, if the requesting party's system 140 is a less specialized general purpose decoding system, such additional information may advantageously be integrated in the transmitted code.

In yet another example of communication with PC 120, the requested information may be communicated to a requesting party without the use of a visual display device whatsoever. For example, in a situation where the requesting party is working away from an office environment, such as an emergency medical technician (EMT) responding to an emergency call, suitable display equipment may not be readily available. Here communication suitable to access the patient's information may be maintained solely through linking telephony devices 150 and 125 through PSN 172. For instance, the EMT in our example may initiate a call through a cellular telephone, telephony device 150, to an interactive voice response unit, telephony device 125, coupled to PC 120. The EMT may speak information necessary to navigate menus offered by PC 120 or may use DTMF signals. PC 120 may then present information retrieved from bulk storage device 122 in an audio format. Such audio presentation of the digital information may be accomplished by the use of text to voice technology well known in the art.

Of course, the presentation of stored information in an audio format may necessitate the inclusion of certain header or caption information to aid the recipient in understanding the information so presented. As discussed above, PC 120 may integrate such information into the information retrieved from bulk storage device 122 prior to its output through telephony device 125.

Having explained the overall operation of the present invention, attention is now directed to FIG. 2, where there is illustrated one method of operation at a patient information origination site. At box 20 a decision is made as to whether this is going to be a manual input system or information already within the system is to be utilized. If the document is to be input manually, it is scanned by process 21. Scanning process 21 may include subprocesses, such as optical character recognition (OCR), to enable the manipulation of textual information contained within the prescription document.

Of course, methods other than scanning may be utilized to manually input the document, such as, for example, keyboard entry or even electronic transfer of information through various means by devices such as another processor-based system. For example, a hand-held or portable processor device may be utilized by a physician when diagnosing a patient and, thereafter, symptom, diagnosis, and/or treatment information transmitted to the system of the present invention. However, it shall be appreciated that scanning a document containing an image is an expedient way to manually input such graphical information into a system.

Thereafter, the input information is used to create a code according to the present invention (process 22). The system may create a code including only information originally input, such as by the physician, or may append additional information. For example, the information scanned by process 21 may have been converted to alpha-numeric information by an OCR process and then coded into a bar code without any manipulation of the information content. Alternatively, the system may integrate other information accessible to the system into the input information. For example, historical information regarding the same patient condition may be integrated into the input information to enable cross referencing of multiple occurrences.

If the determination made at box 21 is that this is not to be a manual system, that is, the computer is to generate the coded information directly, then process 23 would control. Process 23 manipulates the information already found within the system, or readily accessible to it, to generate coded information according to the present invention. For example, patient information may be generated in a word processing system operating on a system in information communication with the process of the present invention. This information may be directly accepted by, and manipulated to be suitable for use in, the present invention. Likewise, graphical information generated by a processor-based system, such as a MRI, may be directly communicated to the system without the need for manual input such as scanning. Here to, the coded information may include not only the input patient information, but may also include additional information as determined advantageous.

After the system creates or generates coded information corresponding to the input information, it is output via process 24. Process 24 may simply output the coded information as generated by the system, or may integrate it within other information to also be output. For example, where the patient information is initially in the form of a document scanned into the system at process 21, the coded information may be integrated into the scanned image of the document and output as the original document having a coded section imposed therein. Similarly, the coded information may be associated with other information, such as a human readable copy of the patient information, and the combination be output.

Alternatively, the coded information may be output without other associated information. Such an embodiment might be preferable where the original information is to be retained at the originating site and only the coded information is to be transmitted to the central storage facility, for example.

Outputting of the coded information may be by any means determined to be advantageous. For example, process 24 may entail printing of the coded prescription in hard copy form to be posted or otherwise physically transmitted to the central storage facility.

Alternatively, process 24 may involve the electronic transmission of the coded information to the central storage facility or other recipient. Such electronic transmission may be by such means as a facsimile device, either coupled directly to the system generating the coded information or indirectly through a hard copy being printed and subsequently input into a "stand alone" facsimile machine. Of course, the receipt of the facsimile transmission may be through a stand alone facsimile machine printing the coded information or may be by a processor-based system adapted to receive facsimile communication directly. Electronic transmission may also be accomplished by such means as processor-based system to processor-based system through a public switched network, local area network, wide area network, or even the Internet.

It shall be appreciated that the output of the coded information by process 24 may include more than a single copy of the code being output. For example one copy may be output for the patient to retain, another to be transmitted to the central storage facility, and yet another output for transmission to an interested third party such as an insurance carrier. Likewise an additional copy may be output for storage at the site generating the patient information.

It shall be understood that where multiple copies of the coded information are output, each copy may include information relevant to its particular use. For example coded information to be provided to the patient may also include human understandable information not included in the coded information as transmitted to the central storage facility.

Furthermore, the means by which different copies of the coded information are output may be different. For example, a copy directed to the patient may be physically printed for hand-delivery to the patient while a copy directed to the central storage facility may be electronically transmitted. It shall be appreciated, that various delivery means may also be utilized for any particular version of the coded information. Depending on the particular central storage facility to receive the coded information, for example, the coded information may be printed or electronically communicated.

Directing attention now to FIG. 3, a preferred method and system at a typical receiving central storage facility is shown. Here, the document containing the coded information is received at process 30. As discussed above, receipt may be via a physical transmission, such as through a postal system, or it could be an electronic transmission. Electronic transmission may involve printing of the document at the recipient central storage facility prior to utilization by the present invention, such as by a fax transmission to a stand alone facsimile device. However, electronic transmission may result in the direct input of the document into a processor-based system at the recipient central storage facility, such as by a fax transmission to a facsimile device coupled to a PC.

If transmission resulting in a hard copy version of the coded information is utilized, the document containing the coded information is then scanned via process 31 such that the coded information may be stored and/or manipulated by the central storage facility's processor-based system. It shall be appreciated that the entire coded document may not necessarily be scanned by process 31. For example, if any human understandable component is included on the document it may be unnecessary for the system's use and, thus, may not be scanned into the system.

Of course, where the coded document is received electronically the document may be directly input at process 31, rather than scanned. The coded information can be stripped from any unnecessary information contained in the electronic transmission, such as human understandable information, and processed by the central storage facility's system.

It shall be appreciated that, where security of stored information is a concern, receiving process 31 may include various sub-processes to verify that the party transmitting the information is authorized to do so.

After its receipt by the central storage facility, the coded information is translated via process 32 for storage and subsequent use by the system. Such translation may entail the conversion of the coded data into a format compatible with the storage system or congruent with that of other stored data. Translation may also involve manipulation of the information, such as merging portions of the coded information with other portions of the coded information or other information available within the system. Of course, where the coded data as scanned or received by the central facility's system is in a form already suitable for storage and use, translation process 35 may be omitted, if desired.

The information is stored for later retrieval and use at process 33. Such storage may include substeps of indexing the stored information to aid in its logical or expedited retrieval when needed. It shall be appreciated that the indexing of the stored information enables the system to more readily identify and access information stored therein. Such an indexing system is useful in managing large volumes of information to present select portions upon specific request of a user.

Now directing attention to FIG. 4, a preferred method and system for disseminating information stored at the central storage facility is shown. Process 40 establishes communication with a site requesting stored information. Of course, where security or confidentiality is a concern the system may provide a substep of verifying that the requesting site is authorized to access the system and/or specific information.

It shall be appreciated that communication established by process 40 may be any means capable of transmitting the stored information. As discussed above, such means may include processor-based systems in information communication, transmission of a facsimile of the stored information, or even may include audio transmission.

However, it shall be understood that, depending upon the type of communication established between a requesting site and the central storage facility, the format of subsequent interaction may be different. For example, where a PC is utilized by a requesting site, interaction with the central storage facility may be in the form of textual menus transmitted to the requesting site anticipating alpha-numeric responses. Thereafter, the patient information may be transmitted in coded form or may be decoded to be presented as textual or graphic image information suitable for display by the requesting site's PC. Where the stored information is transmitted in coded form, it is presumed that a decoding device is available for use at the recipient site. It shall be appreciated that the transmission in coded form may be advantageous as reducing the volume of transmitted data and therefore, more efficiently utilizing the available bandwidth.

Alternatively, where a telephone is utilized by a requesting site, interaction with the central storage facility may be in the form of audio prompts to the requesting site anticipating DTMF or audio responses. Thereafter, the patient information may be presented as a facsimile image or limited portions may be decoded and audibly reproduced. It shall be appreciated that audio reproduction of the information must be limited as any graphic component of the stored information may not be so reproduced. Of course, textual portions may be audibly reproduced and the graphical components transmitted separately, if desired.

Process 41 provides the above mentioned interaction between the requesting site and the central storage facility by accepting information indicating the patient information to be transmitted. The acceptance of such information may, as discussed above, entail various interactions to prompt responses from the requesting party. Of course, where it is envisioned that a requesting party will have sufficient knowledge to formulate a request for information suitable to retrieve the necessary information without such prompting, it may be omitted if desired.

Interaction at process 41 may also include indicating a form of output of the requested information. Of course, the form of information output may default to a particular form based on the connection established or identification of the requesting party, if desired.

Alternatively, rather than the manual input of specific information regarding the information desired, an automated or semi-automated method may be utilized. For example, the requesting party may manipulate a system at the requesting party's site that forms a request suitable to retrieve the requested information from the central storage facility without any further operator interaction.

After accepting information indicating the particular information the requesting site is desirous of, process 42 locates and retrieves the desired patient information. It shall be understood that a process for location and retrieval of information may utilize any number of methods well known in the art to identify stored data responsive to the request in process 41. For example, an index of key words or phrases may be utilized to locate stored patient information suitable for satisfying the requesting party's request. Likewise, a predetermined categorization system may be utilized to identify the patient information for storage and retrieval. Here an information category may be assigned at the time of initial storage which is then utilized at the time of retrieval to output all such categorized information.

Upon selection of stored information to present in response to the requesting party's desires, process 43 determines whether the information as stored must be manipulated in order to properly respond to the request. For example, where the stored information is to be presented in a decoded format, such as the audio format discussed above, process 44 will manipulate the stored patient information to be presented in the desired format.

Likewise, where it is determined that the stored patient data is to be presented for use by a requesting party without any interpretation by a machine or process at the requesting party's site, such as presenting a human understandable facsimile image, certain header or captioning information may be advantageous in the requesting party's understanding of the raw information. Here, before output of the requested information by process 45, process 44 may decode the information and append such identification information as simple explanatory phrases to particular pieces of information so as to identify their context within the transmitted information. Similarly, where, for example, the stored patient information is to be reproduced audibly, process 44 may assemble the words and phrases of the stored information into complete human understandable sentences prior to audio output by a text to speech apparatus by process 44.

However, if process 43 determines that the information as stored may be presented without manipulation, the information is output to the requesting party in the form in which it is stored in by process 45. The output of the stored information without manipulation to meet a particular format may be useful, for example, where the requesting party has established communication with the central storage facility via a processor-based system operating under control of a program compatible with the stored information. Here the stored coded patient information may be output by the storage system in the form it is stored in and manipulated to any desirable format by the requesting party's system. It shall be appreciated that such presentation of the stored information relieves some of the burden upon the central storage facility and distributes it to the requesting site. Furthermore, such decoding by a requesting party site allows for the decoding of the information in a language selectable by the requesting party without the need for storage of multiple languages at the central storage facility.

It shall be understood, although the transmission of a single document has been discussed above, that a transmission in response to a request for information may include multiple documents. For example, where the information is to be transmitted in coded form as originally stored, a request that indicates several entries should be transmitted may result in several coded documents being transmitted to the requesting party.

It shall be appreciated that a substantial portion of the above discussed storage and retrieval of information is automated, minimizing the need for operator interaction. As such, the system and method of the present invention not only reduces the likelihood of transmission of erroneous information but also operates to reduce the time, and therefore the expense, of the transfer of information. Furthermore, as the centralized storage facility of the present invention presents the patient information, or select portions thereof, in a number of different formats, the stored patient information is available to a maximum number of parties desiring such information.

Although the present invention and its advantages have been described in detail, it should be understood that various changes, substitutions and alterations can be made herein without departing from the spirit and scope of the invention as defined by the appended claims.

What is claimed is:

1. A method for creating and storing documents, wherein a group of said documents pertains to a common entity of a plurality of entities, said method comprising the steps of:

bar coding, by a sender, of all data contained in each document including graphics data contained therein, said bar coding to be uniform for all documents and containing a portion pertaining to the identity of an entity of said plurality of entities to which a particular bar coded document pertains;

storing said bar coded documents in at least one electronic data file; and delivering said stored and bar coded documents pertaining to a selected said common entity upon command of an authorized person, wherein said documents are medical records and said common entity is a patient and said authorized person is an attending physician.

2. The method set forth in claim 1 wherein said documents are created at diverse locations by diverse processes under control of different people.

3. The method set forth in claim 2 further comprising the steps of:

receiving a group of delivered bar coded documents; and translating said bar coded documents into medical data pertaining to said patient.

4. The method set forth in claim 3 wherein said translated medical data is in a structure controlled by said authorized person.

5. The method set forth in claim 1 further comprising the step of:

selecting by said authorized person a subset of said data pertaining to said selected entity.

6. The method set forth in claim 1 further comprising the steps of:

receiving a delivered bar coded document; and translating said bar coded document into human understandable form.

7. The method set forth in claim 6 wherein said human understandable form is in a language controlled by a recipient of said bar coded document.

8. The method set forth in claim 1 wherein said bar coding is high density.

9. A system for the transfer of a medical file from one location to another, said system comprising:

means at a sending location for translating medical files into physically observable coded data, wherein ones of said medical files include graphical information and other ones of said medical files include medical history information;

means for physically reproducing said coded data at a recipient's location; and means for translating said reproduced coded data into one or more of the formats selected from the following formats:

a) electronic data for entry into said recipient's graphical display system;

b) human readable form.

10. The system set forth in claim 9 wherein said translation means includes:

means for translation into a format selected by said recipient location regardless of the format used by said sender location.

11. The system set forth in claim 9 wherein said physically observable coded data comprises a bar code.

12. A system for delivering medical files from a first location to a second location, said medical files containing data pertaining to a patient under supervision of a plurality of care providers, said system comprising:

means, controlled by a first care provider, for outputting at least a portion of said medical data in coded form;

means for storing said portion of said medical data in coded form from said first care provider, said means also storing other data pertaining to a particular patient received in coded format from other sources;

means, controlled by said second care provider, for requesting a portion of said medical data stored by said storing means, said requesting means including prompting of said second care provider for a portion of said medical data desired by said second care provider and an electronic address to which to transmit said desired portions of said medical data;

means for retrieving desired portions of said medical data in response to a request by said second care provider;

means for providing said retrieved coded medical data to an electronic address indicated by said second care provider in a format suitable for presentation through a device operable at said electronic address, wherein said format is selected from a group including said medical data in coded form and said medical data in human understandable form; and means, controlled by said second care provider, for receiving said medical data.

13. The system set forth in claim 12 further comprising:

means for outputting said medical data in coded form as a physically observable document.

14. The system set forth in claim 12 wherein said requesting means comprises:

means for presenting voice prompts to said second care provider.

15. The system set forth in claim 14 wherein said requesting means further comprises:

means for responding to information communicated through DTMF signals.

16. The system set forth in claim 12 wherein said means for providing said retrieved coded data comprises:

means for presenting said desired medical data in an audio format.

17. The system set forth in claim 13 wherein said storage means comprises:

means for inputting said coded medical data output as a physically observable document into an electronic memory.

18. The system set forth in claim 17 wherein said storage means stores said coded medical data in its code state.

19. The system set forth in claim 17 wherein said storing means comprises:

means for optically scanning said coded medical data output as a physically observable document.

20. The system set forth in claim 12 wherein said storing means comprises:

means for indexing said coded medical data, said index suitable to be utilized in retrieval of said stored coded medical data.

21. The system set forth in claim 12 wherein said means for providing said retrieved coded medical data comprises:

means for appending additional information to said retrieved portion of said medical data prior to transmission to said second care provider.

22. The system set forth in claim 12, wherein said second care provider's receiving means includes:

means for translating said coded medical data into a selectable human readable language.

23. The system set forth in claim 12 wherein said coded form comprises a bar code.

24. The system set forth in claim 12 wherein said other data pertaining to a particular patient is received in physical coded format from other sources.

* * * * *